United States Patent [19]

Carter

[11] Patent Number: 5,683,655
[45] Date of Patent: Nov. 4, 1997

[54] APPARATUS AND METHOD FOR DISINFECTING WRITING INSTRUMENTS

[76] Inventor: Stephen D. Carter, 1895 Chartwell Trace, Stone Mountain, Ga. 30087

[21] Appl. No.: 563,989

[22] Filed: Nov. 29, 1995

Related U.S. Application Data

[63] Continuation-in-part of Ser. No. 380,087, Jan. 30, 1995, abandoned.

[51] Int. Cl.⁶ .................................................. A61L 2/00
[52] U.S. Cl. ........................... 422/28; 15/104.92; 15/423; 134/6; 422/292; 422/300
[58] Field of Search .......................... 422/28, 292, 300; 15/104.92, 423; 401/9, 10; 134/6, 42

[56] References Cited

U.S. PATENT DOCUMENTS

| 648,928 | 5/1900 | Davis | 211/69 |
|---|---|---|---|
| 1,732,467 | 10/1929 | Gregory | 15/423 |
| 1,748,900 | 2/1930 | Pilla | 15/256.6 |
| 2,121,309 | 6/1938 | Swift | 422/300 X |
| 2,323,615 | 7/1943 | Martineau | 422/300 |
| 3,273,846 | 9/1966 | De Mare | 15/423 |
| 3,393,416 | 7/1968 | Kilpatrick | 15/104.92 |
| 4,530,726 | 7/1985 | Montiel | 134/6 |
| 5,318,030 | 6/1994 | Williams | 422/300 X |

*Primary Examiner*—Robert J. Warden
*Assistant Examiner*—Krisanne M. Thornton
*Attorney, Agent, or Firm*—Bell, Seltzer, Park & Gibson

[57] ABSTRACT

The apparatus of this invention can be used to disinfect a writing instrument used by a health care professional when working with a patient. The apparatus includes an absorbent material pad that has a breach formed, for example, with a slit or a series of slits extending entirely through the pad. The pad is soaked with disinfecting fluid, and a writing instrument is inserted through the breach in the pad to disinfect the writing instrument. To hold the pad in a fixed position, the apparatus includes a holder with first and second members that can be joined together or separated to allow insertion or removal of the pad. The first and second members of the holder define respective apertures that are aligned with the breach in the pad when the first and second members are joined together to enclose the pad. The holder is attached to a body that supports the holder at a sufficiently high level that the writing instrument, when inserted through the pad and the holder, will not be obstructed by the surface upon which the apparatus rests. The apparatus also includes several features to stabilize the apparatus and to minimize spillage or waste of the disinfecting fluid. In addition, the invention includes a related method.

17 Claims, 11 Drawing Sheets

APPARATUS AND METHOD FOR DISINFECTING WRITING INSTRUMENTS

This application is a continuation-in-part of application Ser. No. 08/380,087 filed on Jan. 30, 1995 now abandoned.

BACKGROUND OF THE INVENTION

1. Field of the Invention

This invention is directed to an apparatus and method for disinfecting writing instruments such as pens or pencils used in the practice of dentistry or medicine, for example.

2. Description of the Related Art

Disinfection of instruments used in the practice of medicine and dentistry has received much attention in recent years. The existence of communicable diseases such as Acquired Immune Deficiency Syndrome (AIDS) has heightened both professional and patient awareness regarding the sanitary precautions used by dentist and doctors.

Often in the practice of medicine or dentistry, a health care professional is required to write down information with a writing instrument while working with a patient. There is a concern that the handling of the writing instrument can provide a vehicle for cross-contamination of a patient, that is, that microbes or other infecting matter on the writing instrument, may be transmitted to the patient by the health care professional handling the instrument.

In dentistry, the current preferred practice to sanitize a writing instrument, is to swab the writing instrument with a material pad soaked with a disinfecting solution. This procedure is awkward at best, however, because the health care professional must expend considerable time to soak a piece of material, swab the writing instrument with the piece of material and dry the writing instrument before writing with it. Likewise, sterilization by soaking the writing instrument in a cold boat containing a disinfecting solution is impractical because the health care professional must fish out the instrument from the cold boat and dry off the instrument as well as the fingers or hand if used to retrieve the instrument from the cold boat. Further, the use of an autoclave or the like to disinfect a writing instrument requires considerable time and subjects the instrument to elevated temperatures that are likely to destroy it. Thus, all of the above-described disinfecting procedures have significant disadvantages and require considerable time on the part of the health care professional to the point at which, unfortunately, their practice may be omitted altogether as being too difficult to perform.

Accordingly, there is a need in the dentistry and medical fields for an apparatus and method for readily disinfecting writing instruments without suffering from the disadvantages noted above.

SUMMARY OF THE INVENTION

This invention overcomes the above-described disadvantages. An apparatus in accordance with this invention is used to disinfect a writing instrument used by a healthcare professional when working with a patient. The apparatus includes an absorbent material pad, preferably made of plastic foam material, that absorbs disinfecting fluid such as ethyl alcohol. The pad has first and second sides, and a breach that extends entirely through the pad from its first to its second side, and through which a writing instrument is passed for disinfection.

The apparatus also includes a holder to enclose and hold the pad in a fixed position. The holder includes first and second members that can be selectively joined together or separated to insert or remove the pad. The holder's first member defines a compartment and has a first, partially closed side defining an aperture that communicates with the compartment. The holder's first member also has a second, substantially open side that also communicates with the compartment. The holder's second member has first and second sides, and defines an aperture extending from its first side to its second side. The second member's first side is substantially open and its second side is partially closed and defines the aperture of the second member.

To assemble the apparatus, the pad is inserted through the second, open side of the first member into the compartment of the first member. The first side of the second member is joined to the second side of the first member to enclose the pad between the first and second members. When so enclosed, the pad is situated between the first side of the first member and the second side of the second member, with the breach at the first side of the pad aligned with the aperture in the first member, and the breach at the second side of the pad aligned with the aperture in the second member.

The apparatus of this invention preferably includes a body to which the holder is mounted. The holder is mounted on the body so that the holder is situated at a height sufficiently far above a surface upon which the apparatus rests so that a writing instrument can be inserted through the holder and the pad without obstruction by the surface. Also, the holder is preferably tilted to a degree with respect to the horizontal axis of the body so that at least some of the force exerted when forcing a writing instrument through the breach in the pad will be exerted downward along the vertical axis of the body so that the apparatus will not be tipped over or pushed sideways across the surface upon which the apparatus rests. Also, the apparatus preferably includes a spillage cup mounted to the body at a position beneath the holder, to capture disinfecting fluid that may drip from the holder.

To stabilize the apparatus of this invention, the body is preferably mounted to a base tray that has friction pads at its corners. The base tray also defines an open-topped enclosure into which a weight can be inserted, and to which the body can be fitted to enclose the weight inside of the apparatus. The weight serves to lower the center of gravity of the apparatus so that it will not tend to tip over. The base tray also preferably has a spillage tray that can receive a sponge or the like, that is situated underneath the holder and the spillage cup to capture any disinfecting fluid that may drip from the cup or the holder.

Preferably, the apparatus includes a lid that is fitted to the body to contain disinfecting fluid therein. Also preferred, the lid has a cup defined therein to hold writing instruments after disinfection. When the lid and body are joined together, the lid and body define a primary, main reservoir and a secondary reservoir for containing disinfecting fluid. The primary reservoir can be filled through an aperture in the lid that communicates with the main reservoir, and the aperture can be closed with a stopper when inserted into the aperture. The primary reservoir communicates with the secondary reservoir through a gap defined between the lid and the body. To soak the pad with disinfecting fluid, in one embodiment of the invention, the spillage tray serves as a rocker about which the apparatus can be tilted to fill the secondary reservoir with disinfecting fluid that flows through the gap from the primary reservoir. When returned to its normal, upright position, disinfecting fluid no longer flows between the first and second reservoirs, but the fluid in the secondary reservoir flows through an aperture defined in the body, and into a hole defined in the holder, to soak the pad. In a second embodiment of the invention, a pump is mounted to the lid. The pump has an inlet side coupled to a hose that extends to the disinfecting fluid in the main reservoir, and an outlet side that communicates with the second reservoir to discharge disinfecting fluid into the secondary reservoir when the pump is actuated. The disinfecting fluid in the secondary reservoir flows through an aperture in the body and into the hole in the holder to soak the pad in preparation for disinfecting a writing instrument.

The invention also includes a method for disinfecting a writing instrument. The method includes steps of supplying an absorbent material having first and second sides, and including a breach extending through the absorbent material from its first to its second side, with disinfecting fluid, and a step of holding the absorbent material in a fixed position. The method also includes a step of forcing the writing instrument into the breach at the first side of the absorbent material, through the breach in the absorbent material so that the absorbent material substantially surrounds the writing instrument and the disinfecting fluid is uniformly applied to the writing instrument, and out of the breach at the second side of the absorbent material so that the writing instrument is entirely disinfected by one pass through the breach.

The apparatus and method of this invention provide several advantages relative to the prior art. For example, the writing instrument can be entirely disinfected by forcing the writing instrument through the absorbent material pad in only one direction. This feature of the invention eliminates the need to reverse the orientation of the writing instrument while a portion of it is still contaminated, thus risking recontamination of the writing instrument. Also, the apparatus of this invention is relatively stable due to the tilted orientation of the holder relative to the body that causes at least part of the force exerted when forcing a writing instrument through the pad in the holder, to be directed downward along the vertical axis of the body. The configuration of the base tray and its friction pads also help to prevent the apparatus from sliding over a surface upon which the apparatus rests during use of the apparatus. Moreover, the base tray can include a base tray that receives a weight to lower the center of gravity of the apparatus for stabilization. Also, to reduce spillage and waste of disinfecting fluid, the apparatus includes a secondary reservoir that receives a limited quantity of disinfecting fluid from a primary reservoir defined in the apparatus' body, to soak the pad in the holder. The secondary reservoir can be filled conveniently, in the first embodiment of the invention by tilting the apparatus about a rocker extension of the base tray, and in the second embodiment of the invention, by actuating the pump.

DESCRIPTION OF THE PREFERRED EMBODIMENTS

Figure 1:
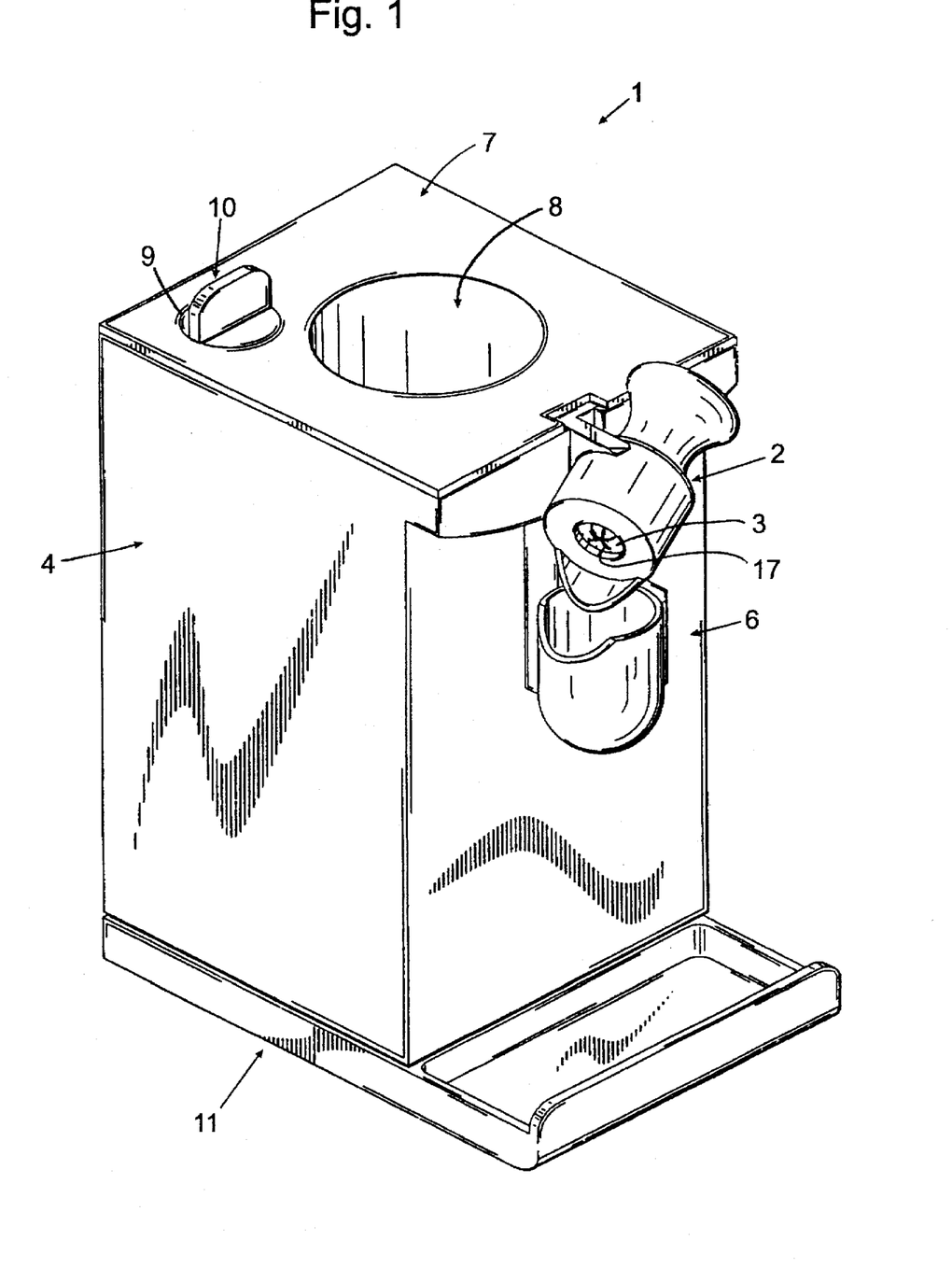
FIG. 1 is a perspective view of an apparatus in accordance with a first embodiment of this invention.

FIG. 1 is a perspective view of an apparatus 1 in accordance with a first embodiment of this invention. In FIG. 1, the apparatus 1 includes a holder 2 that holds an absorbent material pad 3. The holder 2 is coupled to a body 4 that serves to contain a supply of disinfecting fluid 5 (not shown in FIG. 1) to be supplied to the pad 3. A cup 6 for capturing spillage of disinfecting fluid 5 from the holder 2, is mounted to the body 4 at a position beneath the holder 2. The body 4 defines an open-topped enclosure that is covered by a lid 7. The lid 7 includes a writing instrument container 8 for holding writing instruments after disinfection. The lid 7 also defines an aperture 9 through which disinfecting fluid 5 can be poured into the body 4 for containment therein. To prevent disinfecting fluid 5 from escaping the body 4, a stopper 10 can be fitted into the aperture 9. The body 4 is coupled to and rests on a base tray 11. The base tray 11 serves to stabilize the apparatus 1 on a surface such as a table or counter top or the like.

Figure 2:
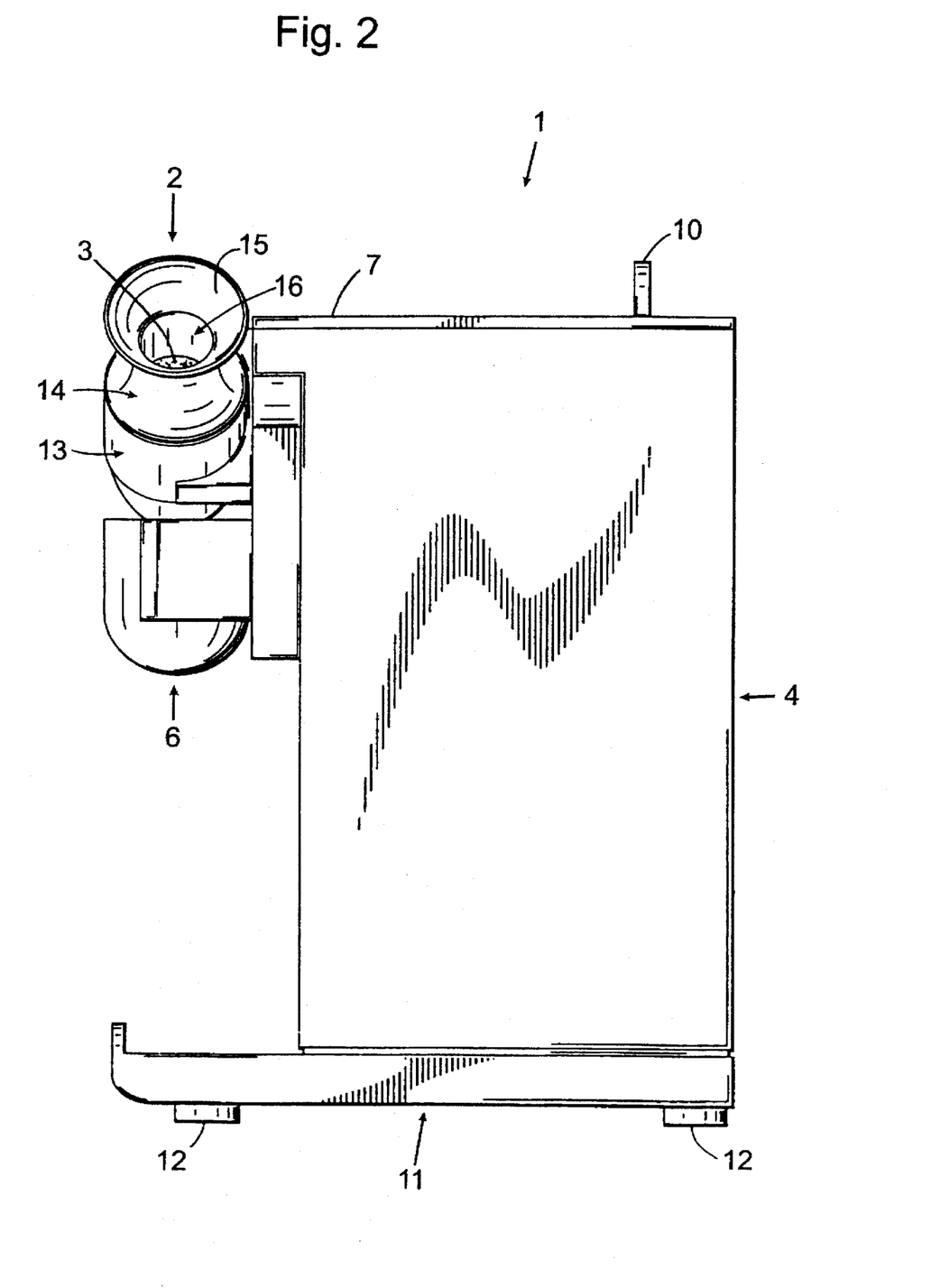
FIG. 2 is a side view of the apparatus of FIG. 1.

FIG. 2 is a side view of the apparatus 1 that is mainly provided herein for an appreciation of the three-dimensional configuration of the apparatus 1. Worth noting in FIG. 2 is that the base tray 11 preferably has a plurality of friction pads 12 that rest against a surface upon which the apparatus 1 sits. The friction pads 12 are preferably formed of a material such as rubber or other plastic material that provides a high degree of friction to prevent the apparatus 1 from slipping on the surface during use of the apparatus. Also noteworthy in FIG. 2 is that the holder 2 includes first and second members 13, 14 between which the pad 3 is contained. The second member 14 has a first side at which is defined a funnel portion 15 for guiding a writing instrument to the pad 3. The second member 14 also has a second side opposite the first side, that contacts the pad 3. Also, the second member 14 defines an aperture 16 that extends from the first side to the second side of the second member 14.

Figure 3:
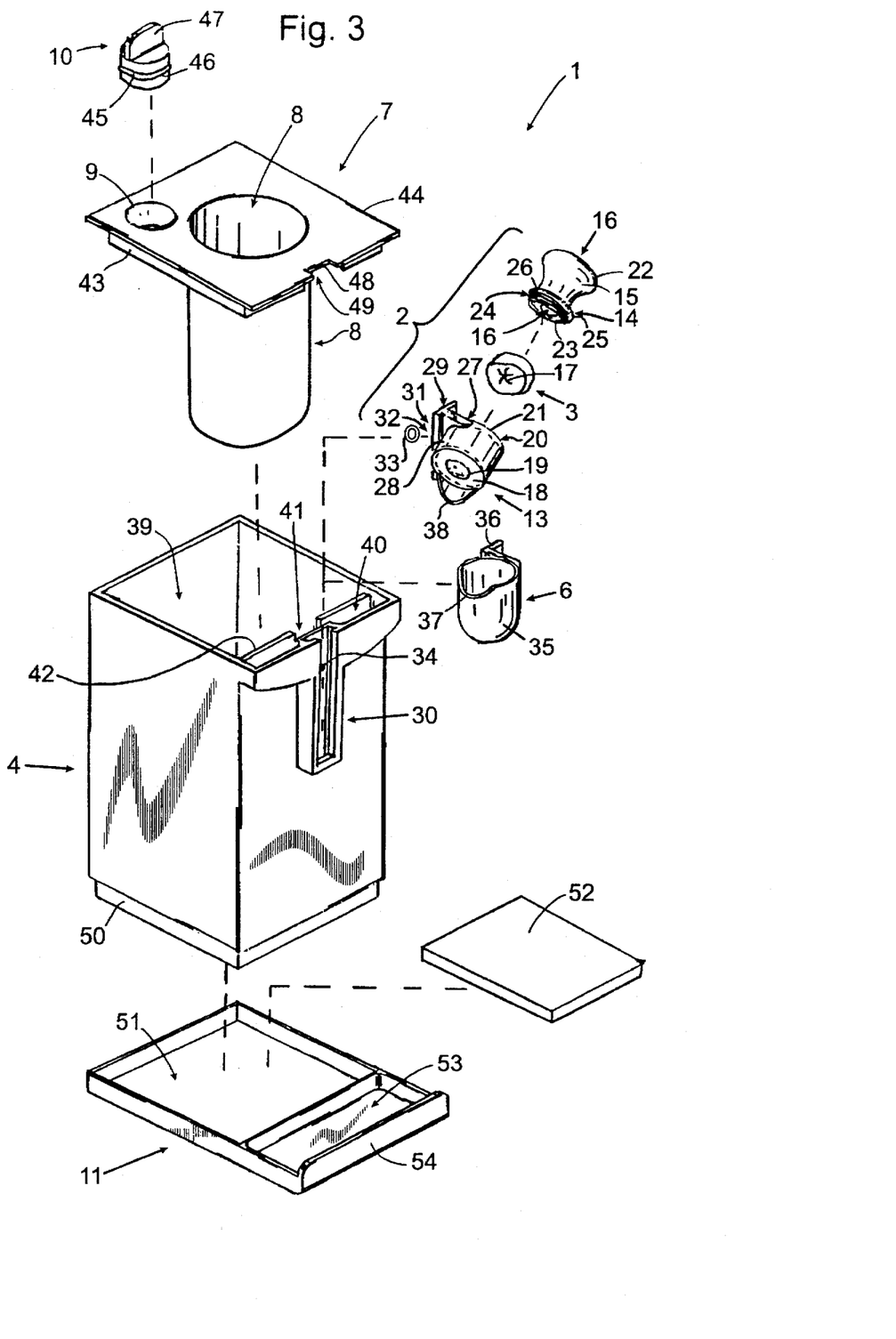
FIG. 3 is an exploded perspective view of the apparatus of FIG. 1.

FIG. 3 is an exploded perspective view of the apparatus 1 of FIG. 1. In FIG. 3, the absorbent material pad 3 has a first side that is visible in FIG. 3, and a second side opposite the first side, that is not visible in FIG. 3 (but which was partially visible in FIG. 2). Preferably, the pad 3 is formed of a material such as foam plastic. The pad 3 defines a breach 17 extending entirely though the pad 3 from its first side to its second side. The breach 17 is formed in the pad 3 by cutting a slit or a series of intersecting slits in the pad 3. The pad 3 serves to absorb disinfecting fluid 5 such as ethyl alcohol, for application to a writing instrument when inserted through the breach 17 in the pad 3.

The apparatus 1 of FIG. 3 also comprises the holder 2 that includes the first and second members 13, 14. The first member 13 has a first, partially closed side 18 that defines an aperture 19 that communicates with an interior compartment 20 (shown with broken lines in FIG. 3) of the first member 13. For example, the compartment 20 can be substantially cylindrical in shape. The compartment 20 communicates with a second, open side 21 of the first member 13 through which the pad 3 can be inserted into or extracted from the compartment 20.

The second member 14 has a first side 22 at which the funnel portion 15 is disposed. The second member 14 also has a second side 23 that is partially closed and that defines the aperture 16 that extends from the first side 22 to the second side 23 of the second member. Also at its second side 23, the second member 14 has an annular extension 24 that is sized to fit snugly in sleeve-like fashion into the second side 21 of the first member 13. The distance to which the annular extension 24 can be inserted into the second side 21 of the first member 13 is limited by an annular rim 25 formed integrally with the extension 24, that is wider in diameter than the outer surface of the extension 24. When the second member 14 is inserted into the first member 13, the rim 25 abuts the second side 21 of the first member 13. To hold together the first and second members 13, 14, the extension 24 has on its outer surface an annular ridge 26 that engages with an annular groove 27 (not shown in FIG. 3) formed inside of the inner wall of the first member 13 that defines the compartment 20. The extension 24 is formed of resilient material that flexes to a degree when the first and second members 13, 14 are joined together until the ridge 26 meets with the annular groove 27 so that the extension 24 returns to its normal, unflexed position with the ridge 26 engaged with the groove 27. The first and second members 13, 14 are thus held together unless pulled apart with sufficient force to move the ridge 26 out of the groove 27.

The holder 2 is assembled by inserting the pad 3 into the second, open side 21 of the first member 13 until the pad 3 contacts the inner surface of the first side 18 with the breach 17 at the first side of the pad 3 being aligned with the aperture 19 in the first side 18 of the first member 13. The pad 3 is thus disposed in the compartment 20 of the first member 13. The second member 14 is joined with the first member 13 in the manner previously described so that the breach 17 at the second side of the pad 3 is aligned with the aperture 16 in the second member 14 and the second side 23 of the second member 14 abuts the second side of the pad 3.

The first member 13 has extending from its outer cylindrical surface 28 a coupler 29. The coupler 29 is elongated in the vertical direction in FIG. 3, and is approximately T-shaped in cross-section. The coupler 29 can be slid into a track 30 defined in the body 4, to engage the holder 2 to the body 4. Although not visible in FIG. 3, the first member 13 defines a hole 31 that extends from the outer side of and through the coupler 29 to communicate with the compartment 20. The first member 13 also defines in proximity to the hole 31 at the outer surface of the coupler 29, a recess 32 (not visible in FIG. 3) that receives an O-ring 33 made of rubber, for example. The O-ring 33 serves as a seal between the hole 31 of the first member 13 and an aperture 34 defined in the track 30 of the body 4 when the coupler 29 is inserted into the track 30 so that the aperture 34 and the hole 31 are aligned.

As previously mentioned, the apparatus 1 includes a spillage cup 6. The cup 6 includes a cup-shaped member 35, and a coupler 36 extending from the outer surface of the member 35. Like the coupler 29 of the first member 13, the coupler 36 is elongated in the vertical direction in FIG. 3 and, in cross-section, is approximately T-shaped. The coupler 36 is mounted to the body 4 by sliding the coupler 36 into the track 30. When the cup 6 is slid into the track 30 and then the first member 13 is slid into the track 30, the cup 6 is positioned beneath the first member 13 to capture disinfecting fluid 5 that may drip from the holder 2. Any disinfecting fluid captured by the cup 6 can be disposed of by removing the cup 6 from the body 4 and pouring out the contents of the cup. To aid in this procedure, the cup 6 preferably has a lip 37 to guide the disinfecting fluid when pouring the fluid from the cup. To channel disinfecting fluid 5 that drips from the holder 2 into the cup 6, the first member 13 preferably includes a slide 38 extending from the first side 18 at a lower edge thereof in FIG. 3. The slide 38 also serves to guide a writing instrument when forced through the holder 2 and the pad 3.

As seen in FIG. 3, the body 4 is an open-topped enclosure. The interior of the body 4 defines a first, primary reservoir 39 for holding the disinfecting fluid 5. The body 4 also defines a second reservoir 40 that communicates with the primary reservoir 39 via a gap 41 defined in a partition 42 situated inside of the body 4. The second reservoir 40 has a relatively small volume and supplies a relatively small amount of fluid 5 to the aperture 34 to soak the pad 3.

The lid 7 is fitted to the open top of the body 4 with an extension 43 that extends from the undersurface of the lid 7, and fits into the open top of the body 4 in sleeve-like fashion. On the top side of the lid 7, the lid has a rim 44 with larger outer dimensions than the extension 43 so that the rim 44 abuts the top edge of the body 4 when the lid 7 is joined with the body 4. When the lid 7 is joined to the body 4 to cover the open top thereof, the aperture 9 defined in the lid 7 communicates with the main reservoir 39 when the stopper 10 is removed from the aperture 9. Through the aperture 9, disinfecting fluid 5 can be poured into the primary reservoir 39.

To seal the fluid 5 in the apparatus 1, the stopper 10 has an O-ring 45 fitted into an annular groove 46 of the stopper 10. The O-ring 45 composed of rubber, for example, forms a fluid-tight seal when inserted into the aperture 9. The stopper 10 also includes a grip 47 so that the stopper 10 can be handled easily with finger tips to insert the stopper into or pull the stopper out of the aperture 9.

When the lid 7 is fitted to the top of the body 4, the under surface of the lid 7 encloses the first and second reservoirs 39, 40 and the writing instrument container 8 fits into the body 4. The undersurface of the lid 7 also closes the top of the gap 41 so that an aperture communicating with the first and second reservoirs 39, 40 is defined between the surfaces of the partition 42 that define the gap 41 and the undersurface of the lid 7. The top surface of the lid 7 has a notch 48 defined therein. When the lid 7 is joined with the body 4, the notch 48 allows passage of the couplers 29, 36 of the first member 13 and the cup 6, respectively, when inserted into the track 30. The lid 7 also has a gap 49 defined therein that provides clearance for the track 30 when the lid 7 is joined with the body 4.

On its bottom side, the body 4 has an extension 50 depending therefrom, that fits into the open top of a weight tray 51 defined in the base tray 11. The tray 51 is an open-topped enclosure that receives a weight 52. The weight 52 is made of dense material such as metal, and is sized to fit into the tray 51. When the weight 52 is inserted into the tray 51 and the extension 50 of the body 4 is fitted into the tray 51, the weight 52 is enclosed in the apparatus 1. The weight 52 serves to lower the center of gravity of the apparatus 1 so that the apparatus is stable and cannot be easily tipped over, a situation that could cause the lid 7 to separate from the body 4 resulting in spillage of the fluid 5.

The base tray 11 also defines a spillage tray 53 that is an open-topped enclosure situated to catch drippage or spillage of disinfecting fluid 5 from the holder 2 and/or the cup 35 when joined to the body 4. The tray 11 can receive a sponge (not shown) if desired to absorb spillage of the fluid 5 from the holder 2 and/or cup 6. The tray 53 is defined by a rocker extension 54 about which the apparatus 1 can be pivoted to tip the apparatus 1 onto its side for reasons to be described in detail later in this document.

Preferably, the body 4, the cup 6, the lid 7, the stopper 10, the base tray 11 and the first and second members 13, 14 are made of plastic material such as polyvinyl chloride or other suitable plastic.

The apparatus 1 is assembled and prepared for use as follows, for example. The weight 52 is inserted into the tray 51 and the extension 50 of the body 4 is inserted into the open top of the base tray 11 to enclose the weight. The lid 7 is joined to the open top of the body 4. The disinfecting fluid 5 is then poured into body 4 through the aperture 9 to fill the reservoir 39. The O-ring 45 is then fitted into the groove 46 of the stopper 10. The stopper 10 is then inserted into the aperture 9 to contain the fluid 5 in the body 4. The coupler 36 of the cup 6 is slid into the track 30 of the body 4. The holder 2 is assembled by inserting the pad 3 into the compartment 20 of the first member 13, and the first and second members 13, 14 are joined together to enclose the pad 3 in the holder 2. The O-ring 33 is then inserted into the recess 32 defined in the first member 13 and the coupler 29 is slid into the track 30 to abut the top side of the coupler 36 of the cup 6. When so positioned, the hole 31 in the coupler 29 is aligned with the aperture 34 in the body 4, and the hole 31 and the aperture 34 communicate inside of the O-ring 33 that seals and prevents leakage of fluid 5 from between the coupler 29 and a surface of the track 30 adjacent the aperture 34.

Figure 4A:
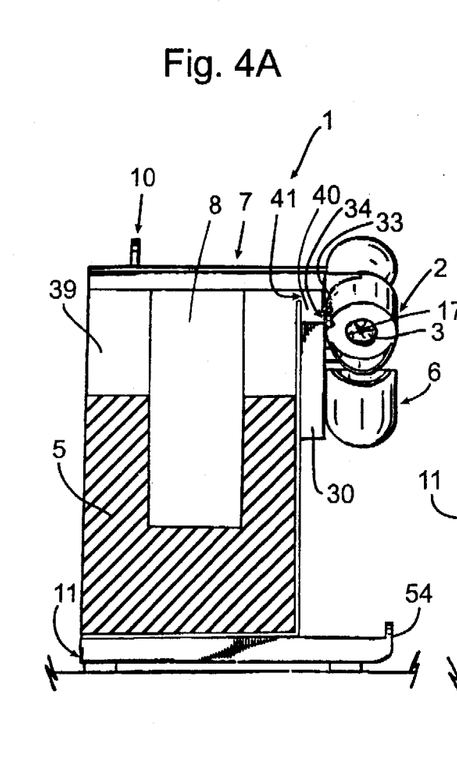
FIGS. 4A, 4B, and 4C are partial cross-sectional views of a sequence of operations to supply disinfecting fluid to an absorbent material pad of the apparatus shown in FIG. 1.
Figure 4B:
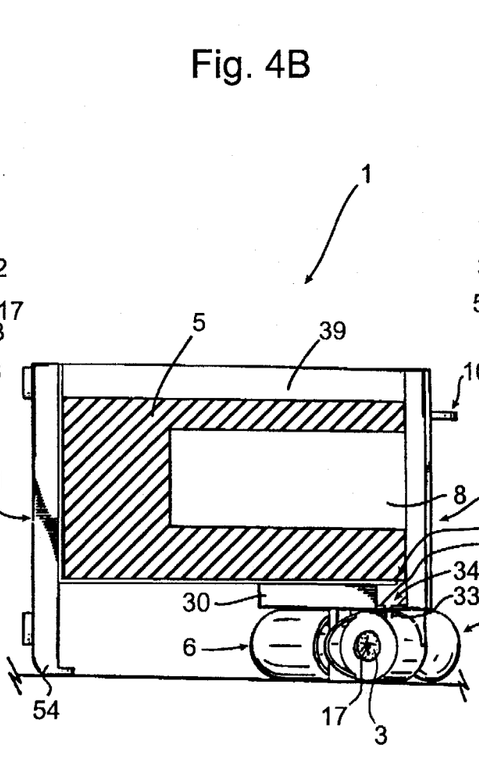
Figure 4C:
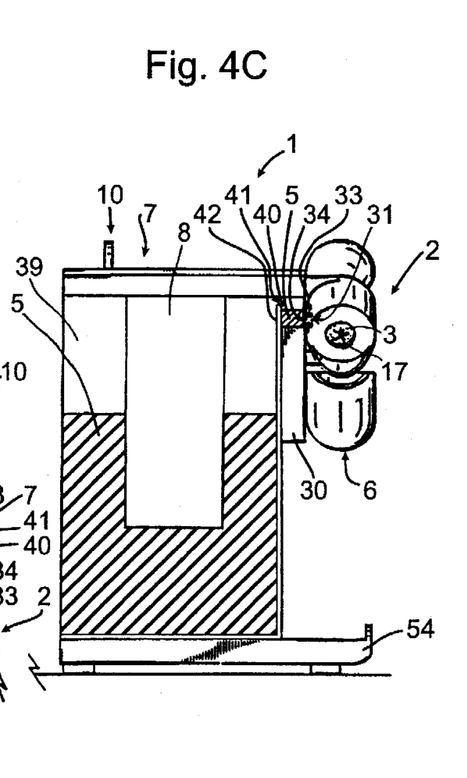

FIG. 4A is a partial cross-sectional view showing the apparatus 1 after filling the reservoir 39 with the disinfecting fluid 5. The apparatus 1 is then tipped about the rocker extension 54 onto its side, as shown in FIG. 4B. Because the rocker extension 54 extends from the apparatus 1 for substantially the same distance as the holder 2 and the cup 6, the apparatus 1 rests approximately along the horizontal direction in FIG. 4B. In the tilted position in FIG. 4B, the fluid 5 flows from the reservoir 39 to the reservoir 40, through the gap 41 and into the reservoir 40. The reservoir 40 is thus filled with the fluid 5. When the apparatus 1 is righted to its normal, upright position in FIG. 4C, fluid 5 is trapped in the second reservoir 40 by the partition 42. Therefore, when the apparatus 1 is righted to its normal, upright position, the reservoir 40 is filled to a volume determined by the height of the partition 42 at the gap 41. The fluid 5 in the reservoir 40 flows through the aperture 34, the O-ring 33 and the hole 31, and soaks the pad 3 in the compartment 20 of the holder 2. The apparatus 1 is thus prepared to disinfect a writing instrument. The volume of the fluid 5 supplied to the pad 3 from the reservoir 40 is preferably sufficient to soak the pad 3, but not so much as to cause appreciable leakage after saturation of the pad 3. The pad 3 can thus be soaked to a degree sufficient to disinfect several writing instruments.

Figure 5A:
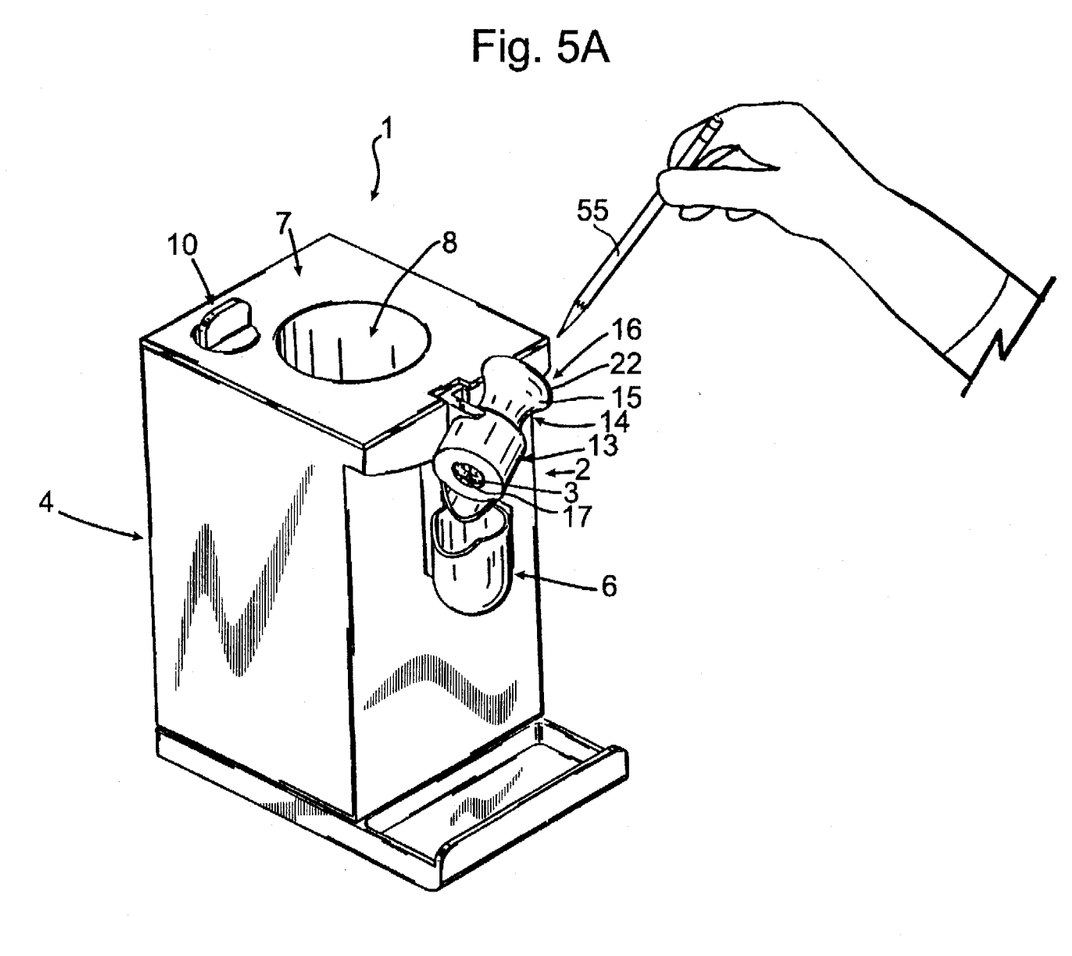
FIG. 5A, 5B, 5C, 5D, and 5E are perspective views of a sequence of operations for disinfecting a writing instrument.
Figure 5B:
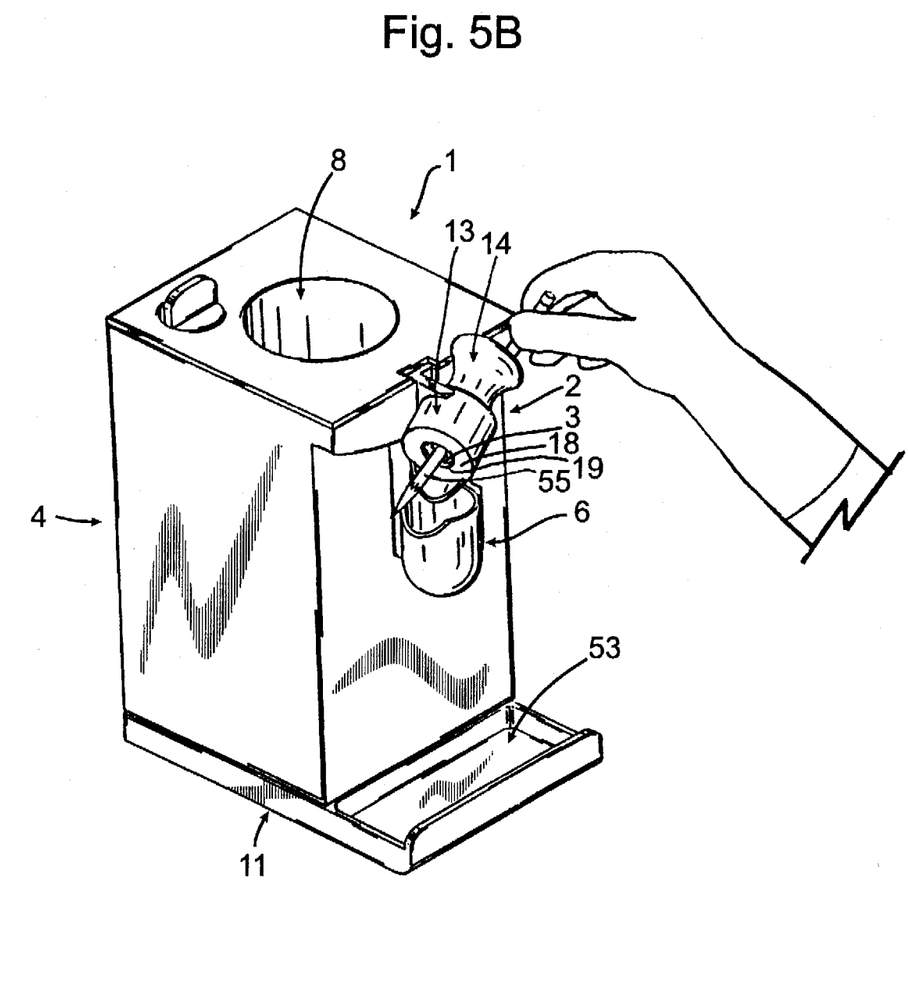
Figure 5C:
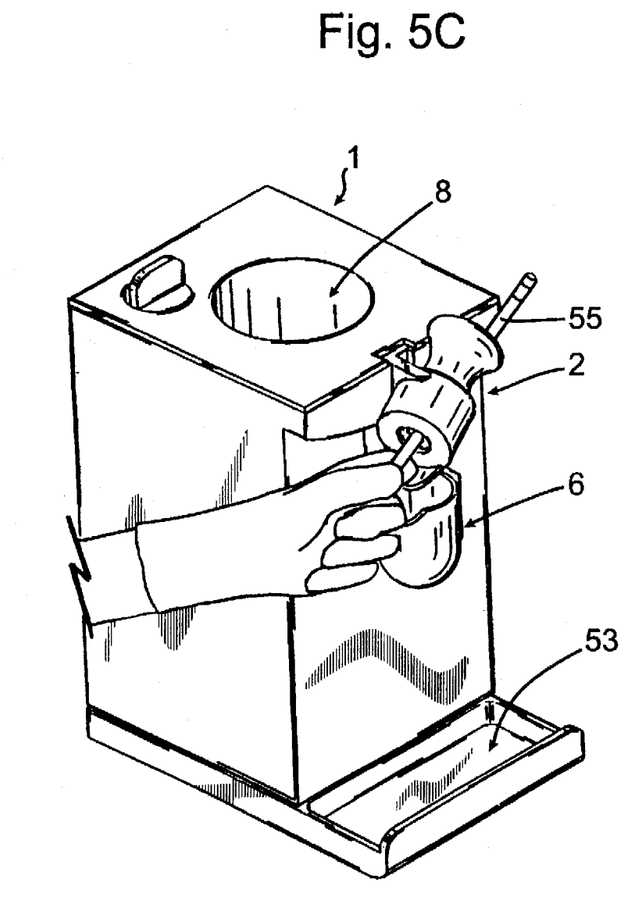
Figure 5D:
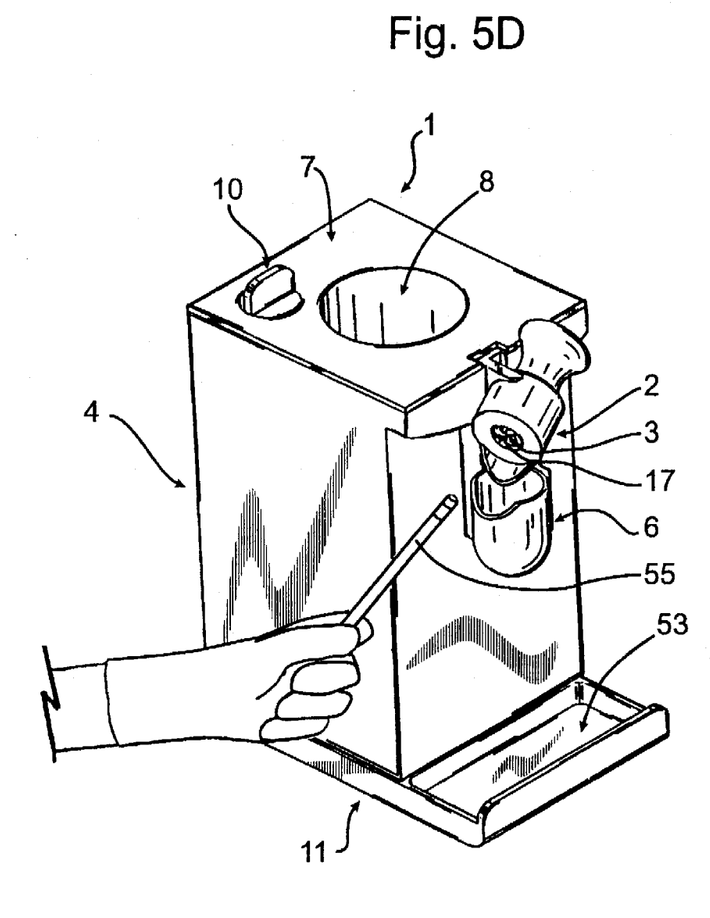
Figure 5E:
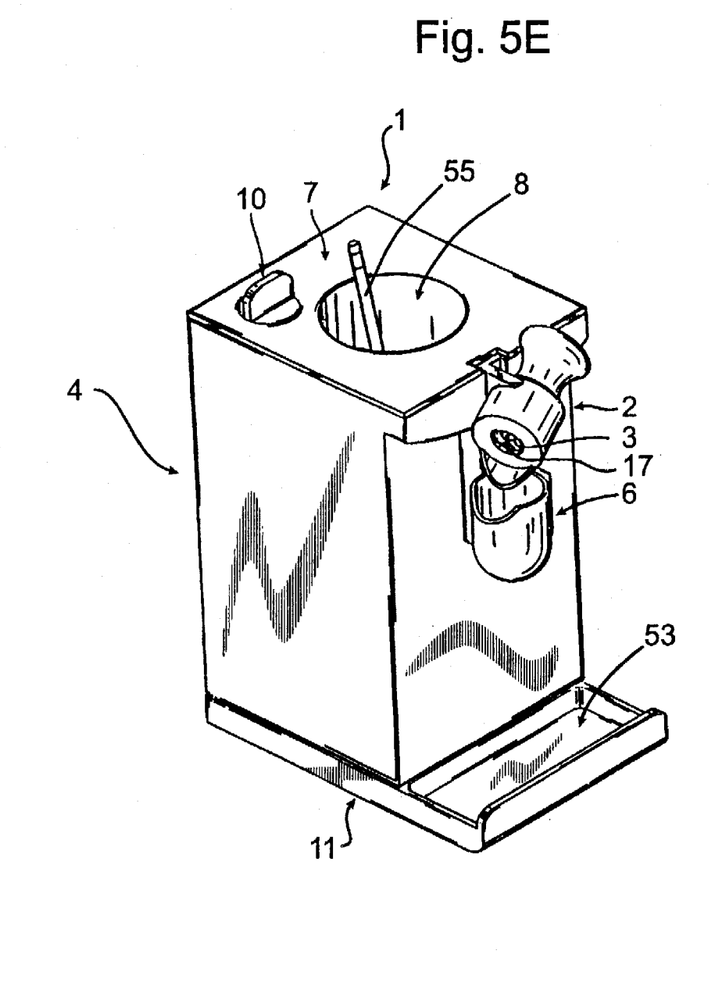

FIGS. 5A–5E are a sequence of views illustrating the operations for disinfecting a writing instrument 55. In FIG. 5A, the writing instrument 55 is forced by hand into the aperture 16 at the first side 22 of the second member 14. The funnel portion 15 guides the writing instrument 55 toward the pad 3 at the second side 23 of the second member 13. The writing instrument is further forced into the breach 17 at the second side of the pad 3, through the pad 3, and out of the breach at the first side of the pad 3. Upon further forcing the writing instrument 55 through the holder 2 and the pad 3, the leading end of the writing instrument 55 passes through the aperture 19 defined in the first side 18 of the first member 13, as shown in FIG. 5B. Any spillage or drippage caused by forcing the writing instrument 55 through the holder 2 and pad 3 is captured by the cup 6 or the spillage tray. Also worth noting in FIG. 5B is that the longitudinal axis of the holder 2 is tilted downward with respect to the horizontal axis of the body 4. Thus, when forcing the writing instrument through the holder 2 and the pad 3, the force is directed vertically downward to a degree sufficient that the apparatus 1 is not pushed in the horizontal direction across the surface upon which the apparatus 1 rests. In FIG. 5C, the leading end of the writing instrument 55 is grasped by hand. Preferably, to avoid recontamination of the writing instrument 55, a sanitized glove is worn on the hand used to grasp the writing instrument. The writing instrument 55 is then pulled the rest of the way through the holder 2 to disinfect the entire writing instrument, as shown in FIG. 5D. The writing instrument 55 can then be inserted into the container 8 for storage until needed as shown in FIG. 5E. Of course, to prevent recontamination of the writing instrument, the container 8 as well as the surfaces of the apparatus 1 should be treated with disinfecting fluid 5 before using the container 8 to hold the writing instrument 55 after disinfection. In the sequence of operations of FIGS. 5A–5E, it will be appreciated that disinfection of the writing instrument 55 is accomplished by forcing the writing instrument through the holder 2 and the pad 3 in one direction. The writing instrument 55 is thus disinfected with a one pass technique that is quick and easy to perform.

Figure 6:
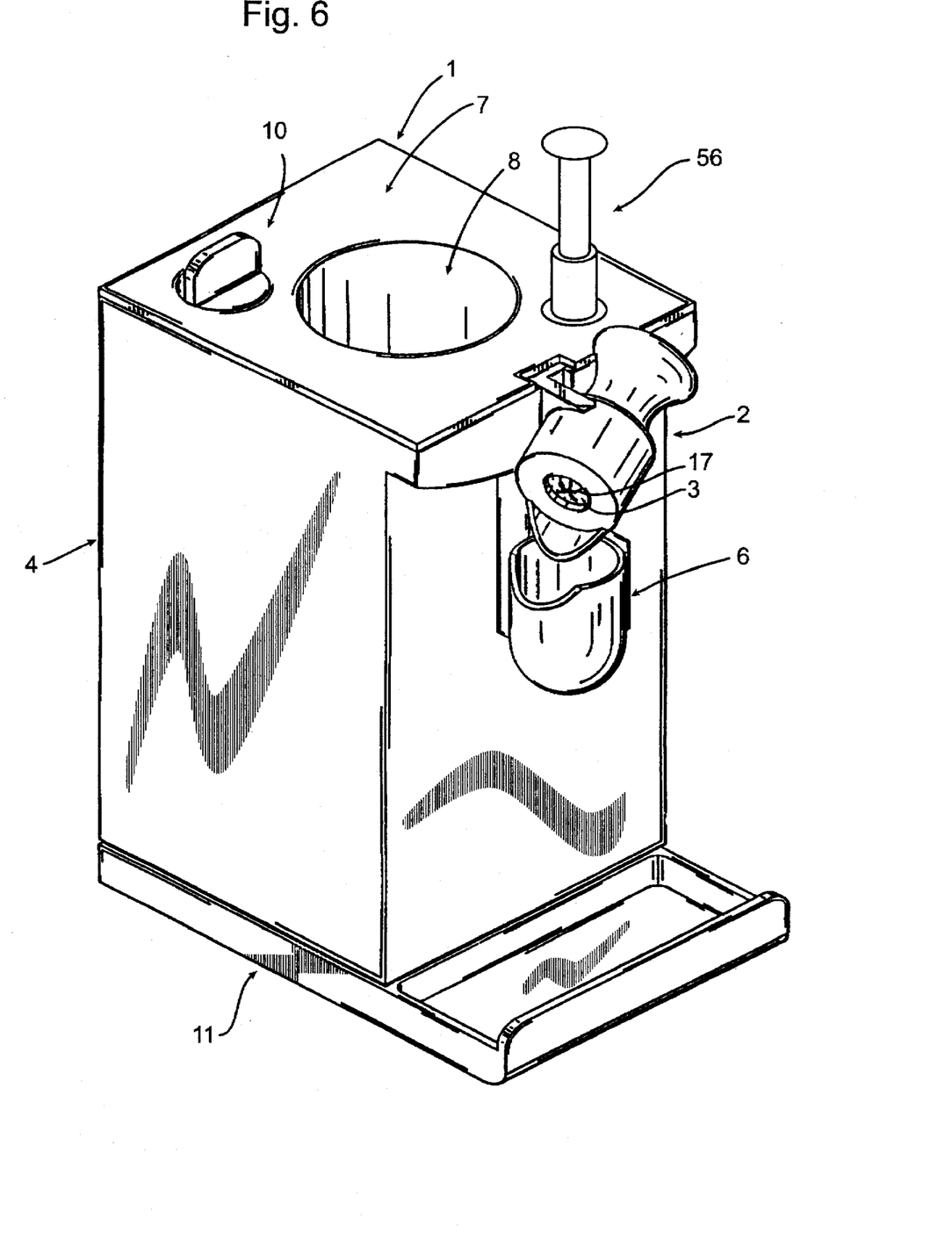
FIG. 6 is a perspective view of an apparatus in accordance with a second embodiment of this invention.
Figure 7:
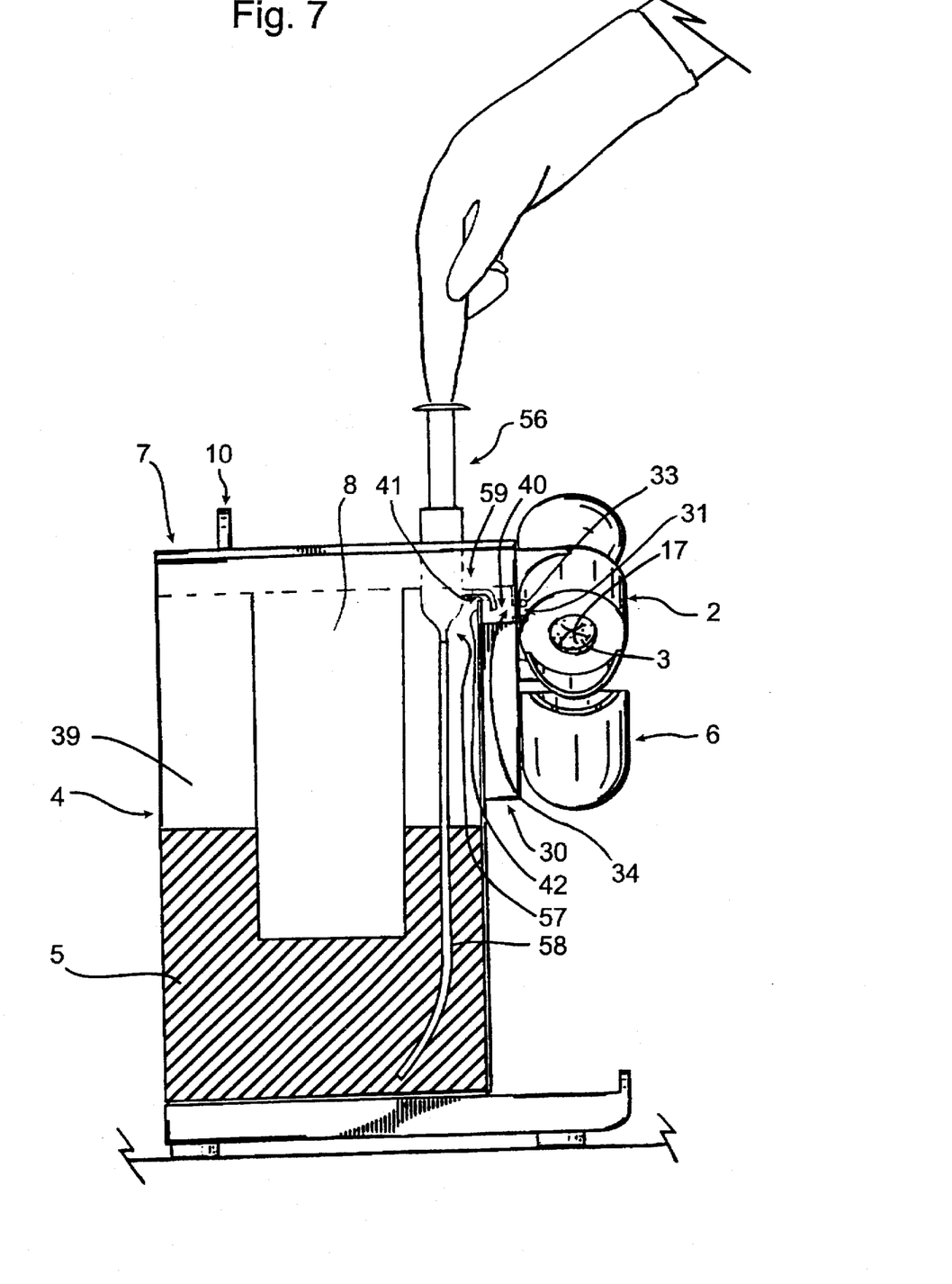
FIG. 7 is a partial cross-section view of the apparatus of FIG. 6, showing the operation of a pump to supply disinfecting fluid to an absorbent material pad of the apparatus.

FIG. 6 is an apparatus 1 in accordance with a second embodiment of this invention. The apparatus 1 of FIG. 6 is similar in most respects to the apparatus 1 of FIG. 1, but in addition, includes a pump 56. The pump 56 can be a pump such as those used in conventional pump spray containers. The pump 56 is attached to the lid 7 in a position overlying the reservoir 39. More specifically, as shown in the partial cross-sectional view of FIG. 7, the pump 56 has an inlet side 57 coupled to a hose 58, and an outlet side 59 communicating with the reservoir 40. To deliver fluid 5 to the reservoir 40, the pump 56 can be finger-actuated, for example, by pushing down and releasing the pump. When so actuated, the pump 56 draws fluid 5 from the reservoir 39 via hose 58 that is drawn into the inlet side 57 of the pump 56, and this fluid 5 is discharged from the outlet side 59 of the pump into the reservoir 40. The fluid 5 in the reservoir 40 flows by gravity through the aperture 34, the O-ring 33, into the hole 31 and into the compartment 20 to soak the pad 3 contained therein. If desired, the pump 56 can be such that, when actuated, a predetermined quantity of the fluid 5 is delivered to the reservoir 40 to minimize spillage of disinfecting fluid from the holder 2.

The apparatus 1 of FIG. 6 is assembled by attaching the pump 56 to the lid 7 and coupling the hose 58 to the inlet side 57 of the pump 56. The loose end of the hose 58 is then inserted into the reservoir 39 of the body 4, and the outlet side 59 of the pump 56 is positioned to extend through the gap 41 in the partition 42 so that the outlet side 59 communicates with the reservoir 40. The stopper 10 is then removed from the lid 7 and the disinfecting fluid 5 is poured through the aperture 9 and into the reservoir 39 to a level sufficient to submerge the end of the hose 58. The stopper 10 is then fitted into the aperture 9 to contain the fluid 5 in the body 4. The remaining assembly of the apparatus 1 is the same as that previously described with respect to the apparatus 1 of FIG. 10. The preparation of the apparatus 1 of FIGS. 6 and 7 for disinfecting a writing instrument is relatively simple, requiring only the actuation of the pump 56 to draw fluid 5 from the reservoir 39, and to discharge the fluid 5 into the reservoir 40. Accordingly, the steps of FIGS. 4A–4C described with respect to the apparatus 1 of FIG. 1, are not necessary with the apparatus 1 of FIGS. 6 and 7. However, the operation of the apparatus 1 of FIGS. 6 and 7 to disinfect a writing instrument is the same as that previously described with respect to FIGS. 5A–5E.

Although the invention has been described with specific illustrations and embodiments, it will be clear to those of ordinary skill in the art that various modifications may be made therein without departing from the spirit and scope of the invention as outlined in the following claims.

I claim:

1. An apparatus for disinfecting a writing instrument with a disinfecting fluid, the apparatus comprising:

an absorbent material pad having first and second sides, and a breach extending through the pad from the first side to the second side of the pad, the pad absorbing the disinfecting fluid;

a holder including a first member defining a compartment, the first member having a first, partially closed side defining an aperture that communicates with the compartment, and a second, substantially open side communicating with the compartment, and a second member joinable with and removable from the first member, the second member having first and second sides, and defining an aperture extending through the second member from the first side to the second side of the second member, the second side of the second member being partially closed so that, when the pad is inserted through the second, open side of the first member into the compartment of the first member and the second side of the second member is joined to the second side of the first member to assemble the apparatus, the pad is contained and held between the first side of the first member and the second side of the second member with the breach at the first side of the pad aligned with the aperture in the first side of the first member and the breach at the second side of the pad aligned with the aperture in the second member, the writing instrument being disinfected by forcing the writing instrument into the aperture of the second member, into the breach at the first side of the pad, through the pad, out of the breach at the second side of the pad, and out of the aperture of the first member.

2. An apparatus as claimed in claim 1, wherein the first member defines a hole extending between an outer surface of the first member and the compartment, the apparatus further comprising:

a body to which the holder is mounted, the body being an open-topped enclosure, the body defining first and second reservoirs for containing the disinfecting fluid, the first reservoir communicating with the second reservoir and the second reservoir communicating with the hole in the first member, the second reservoir supplying disinfecting fluid to the hole for absorption by the pad; and a lid adapted to be joined with the body to cover the open top of the enclosure of the body to contain fluid in the first and second reservoirs.

3. An apparatus as claimed in claim 2, wherein the body has a track and the first member includes a coupler, the first member being attached to or removed from the body by sliding the coupler of the first member into or out of the track.

4. An apparatus as claimed in claim 3, wherein, when the coupler of the first member is inserted into the track, the holder is positioned with a longitudinal axis of the holder rotated about a horizontal axis of the body so that the first member is at a generally lower elevation compared to the second member, the holder thus being oriented so that the forcing of the writing instrument through the breach directs at least a part of the force downward along a vertical axis of the body.

5. An apparatus as claimed in claim 3, further comprising:

a cup having a coupler, and mountable in the track with the coupler of the cup so that the cup is disposed in a position beneath the holder, the cup for capturing spillage of disinfecting fluid from the holder.

6. An apparatus as claimed in claim 5, further comprising:

a base tray coupled to a bottom side of the body and having a spillage tray disposed in a position beneath the holder and the cup.

7. An apparatus as claimed in claim 6, wherein the portion of the base tray defining the spillage tray includes a rocker extension about which the body can be tilted between a first, upright position in which the disinfecting fluid is trapped and prevented from flowing between the first and second reservoirs, and a second, tilted position in which the disinfecting fluid flows from the first reservoir to the second reservoir, the second reservoir supplying the disinfecting fluid to the pad.

8. An apparatus as claimed in claim 2, further comprising:

a base tray defining an open-topped enclosure;

a weight situated in the enclosure of the base tray; and a bottom side of the body being adapted to fit into the open-topped enclosure of the base tray in sleeve-like fashion to contain the weight in the base tray.

9. An apparatus as claimed in claim 2, wherein the lid has an aperture formed therethrough that communicates with the first reservoir, for allowing disinfecting fluid to be poured into the first reservoir, further comprising:

a stopper insertable into and removable from the aperture in the lid, the stopper blocking the aperture in the lid to prevent disinfecting fluid from escaping from the body when the stopper is inserted into the lid.

10. An apparatus as claimed in claim 2, wherein, when the body is tilted from its upright position to a tilted position lying on its side, the disinfecting fluid flows from the first reservoir through a gap defined in the body, to the second reservoir; and wherein, when the body is righted from the tilted position to the upright position after tilting the body on its side, fluid is trapped and prevented from flowing between the first and second reservoirs, the fluid in the second reservoir draining by gravity into the hole of the first member to flow to the pad in the compartment of the first member.

11. An apparatus as claimed in claim 1, wherein the first member defines a hole extending between an outer surface of the first member and the compartment, the apparatus further comprising:

a body to which the holder is mounted, the body defining an open-topped enclosure with a first reservoir containing disinfecting fluid and a second reservoir communicating with the hole in the first member;

a lid adapted to be joined with the body to cover the open top of the enclosure of the body; and a pump mounted to the lid, and having an inlet side communicating with the disinfecting fluid in the first reservoir and an outlet side communicating with the second reservoir, the pump being operable to draw disinfecting fluid from the first reservoir into its inlet side, and being operable to discharge the fluid into the second reservoir, the disinfecting fluid discharged into the second reservoir by the pump draining through the hole in the first member into the compartment for absorption by the pad.

12. An apparatus as claimed in claim 11, wherein the pump is operable to discharge a predetermined amount of disinfecting fluid to the second reservoir.

13. An apparatus as claimed in claim 1, wherein the first holder has a slide extending from the first side of the first member in proximity to the aperture in the first side of the first member, for guiding a writing instrument forced out of the breach at the second side of the pad.

14. An apparatus as claimed in claim 1, wherein the second member includes a funnel portion at the first side of the second member.

15. A method for disinfecting a writing instrument, the method comprising the steps of:

(a) supplying an absorbent material having first and second sides, including a breach extending through the absorbent material from the first side to the second side, with a disinfecting fluid;

(b) holding the absorbent material in a fixed position; and (c) forcing a writing instrument into the breach at the first side of the absorbent material, through the breach in the absorbent material so that the absorbent material substantially surrounds the writing instrument and the disinfecting fluid is uniformly applied to the writing instrument, and out of the breach at the second side of the absorbent material;

the writing instrument being entirely disinfected by one pass through the breach in said step (c).

16. A method as claimed in claim 15, further comprising the step of:

(d) forming the breach in the absorbent material.

17. A method as claimed in claim 16, wherein said step (d) includes a substep of cutting at least one slit in said absorbent material.

* * * * *